US00PP29682P3

(12) United States Plant Patent
Robb

(10) Patent No.: US PP29,682 P3
(45) Date of Patent: Sep. 18, 2018

(54) ***RHAPHIOLEPIS INDICA* PLANT NAMED 'PC2'**

(50) Latin Name: *Rhaphiolepis indica*
Varietal Denomination: PC2

(71) Applicant: John Robb, Kariong (AU)

(72) Inventor: John Robb, Kariong (AU)

(73) Assignee: The Paradise Seed Company Pty. Ltd. (AU)

( * ) Notice: Subject to any disclaimer, the term of this patent is extended or adjusted under 35 U.S.C. 154(b) by 0 days.

(21) Appl. No.: 15/530,331

(22) Filed: Dec. 23, 2016

(65) Prior Publication Data

US 2018/0184558 P1 Jun. 28, 2018

(51) Int. Cl.
*A01H 5/00* (2018.01)
*A01H 5/02* (2018.01)

(52) U.S. Cl.
USPC ..... Plt./254
CPC ..... *A01H 5/02* (2013.01)

(58) Field of Classification Search
USPC ..... Plt./254, 226
See application file for complete search history.

*Primary Examiner* — Susan McCormick Ewoldt
(74) *Attorney, Agent, or Firm* — Cassandra Bright

(57) ABSTRACT

A new and distinctive *Rhaphiolepis indica* plant, characterized by its attractive colored newly emerged immature leaf color corresponding to grayed orange (RHS 177B-C), combined with a well branched, bushy plant growth habit and white flowers produced late winter to spring. The new plant is a *Rhaphiolepis*, normally useful as a landscape plant.

7 Drawing Sheets

Latin name of the genus and species: *Rhaphiolepis indica*. Variety denomination: 'PC2'.

BACKGROUND OF THE INVENTION

The present invention relates to a new and distinct variety of evergreen perennial *Rhaphiolepis indica*, which has been named 'PC2'. *Rhaphiolepis indica* is a medium sized shrub that is used as an ornamental plant in landscape and amenity horticulture. Short, compact forms of *Rhaphiolepis indica* have been selected previously for use in landscape and ornamental horticulture.

The cultivar 'PC2' was discovered in 2011 in Laurieton, New South Wales, Australia, during a seedling selection of cultivated seedlings of the parent variety, an unnamed, unpatented *Rhaphiolepis indica*. Approximately 500 seeds were sown in 2009, which had been collected from the parent variety.

The new variety 'PC2' was first asexually propagated by vegetative cuttings at a commercial nursery in Kulnura, in the state of New South Wales, Australia. Subsequent propagation has shown the features of the new variety are stable and reproduced true to type.

SUMMARY OF THE INVENTION

'PC2' is a distinctive variety of *Rhaphiolepis indica*, which is characterized by its attractively colored newly emerged immature leaf color corresponding to grayed orange (RHS 177B-C), combined with a well branched, bushy plant growth habit and white flowers produced late winter to spring, in New South Wales, Australia. in 2012. The distinctive characteristics of cultivar 'PC2' have remained stable and true to type through successive cycles of asexual propagation.

PARENT COMPARISON

The parent form is characterized by an upright and bushy plant growth habit with weak anthocyanin coloration of the young shoot after flowering. 'PC2' has attractive newly emerged immature leaf color corresponding to grayed orange (RHS 177B-C), not seen in the parent variety. The parent variety is not as well branched as 'PC2'.

COMMERCIAL COMPARISON

'PC2' can be compared to the *Rhaphiolepis* variety 'Fergusonii' (not patented). 'PC2' has strong anthocyanin coloration of the young shoot growth after flowering whereas 'Fergusonii' has weak anthocyanin coloration of the young shoot growth after flowering. 'PC2' has weak undulation of the leaf margin whereas 'Fergusonii' has strong undulation of the leaf margin. 'PC2' has a straight longitudinal leaf axis whereas 'Fergusonii' has a recurved longitudinal leaf axis. 'PC2' has a weak degree of fruit set whereas 'Fergusonii' has a strong degree of fruit set. 'PC2' flowers have filaments with a strong degree of anthocyanin coloration whereas 'Fergusonii' flowers have filaments with a weak to medium degree of anthocyanin coloration.

'PC2' can also be compared to the *Rhaphiolepis* 'Oriental Pearl' (not patented). 'PC2' has strong anthocyanin coloration of the young shoot growth after flowering whereas 'Oriental Pearl' has weak to medium anthocyanin coloration of the young shoot growth after flowering. 'PC2' has early to medium time of flowering whereas 'Oriental Pearl' has medium time of flowering. 'PC2' has a broad leaf width whereas 'Oriental Pearl' has a medium leaf width. 'PC2' has an elliptic leaf shape whereas 'Oriental Pearl' an obovate leaf shape.

DESCRIPTION OF THE DRAWINGS

This new *Rhaphiolepis* is illustrated by the accompanying photographs which show the plant's form, foliage, flowers and fruit. The colors shown are as true as can be reasonably obtained by conventional photographic procedures. Plants were grown in New South Wales, Australia.

BOTANICAL DESCRIPTION OF THE VARIETY

Figure 1:
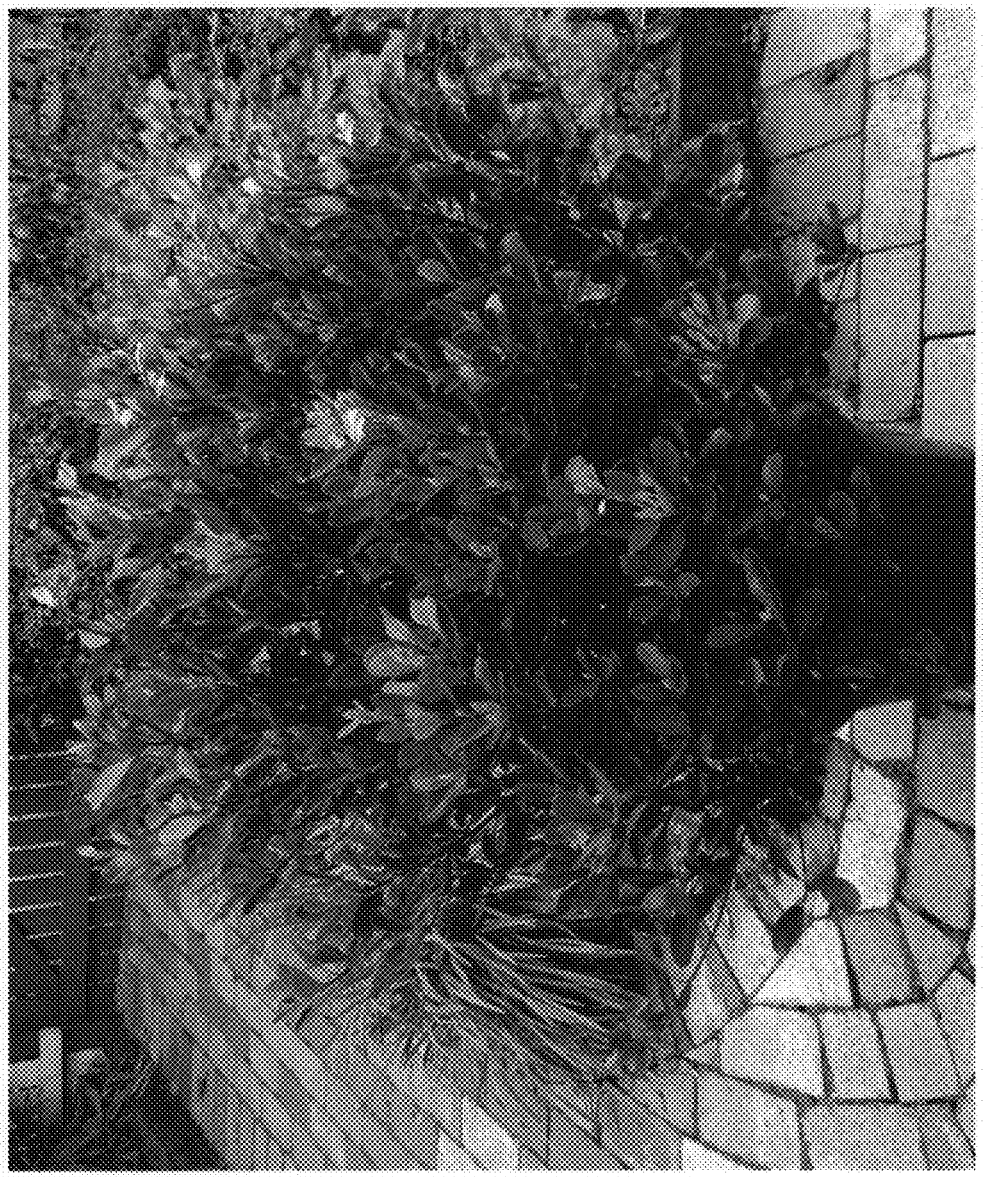
FIG. 1 shows the bushy plant growth habit and emerging new shoot growth color of a *Rhaphiolepis indica* 'PC2' plant at approximately 24 months of age.
Figure 2:
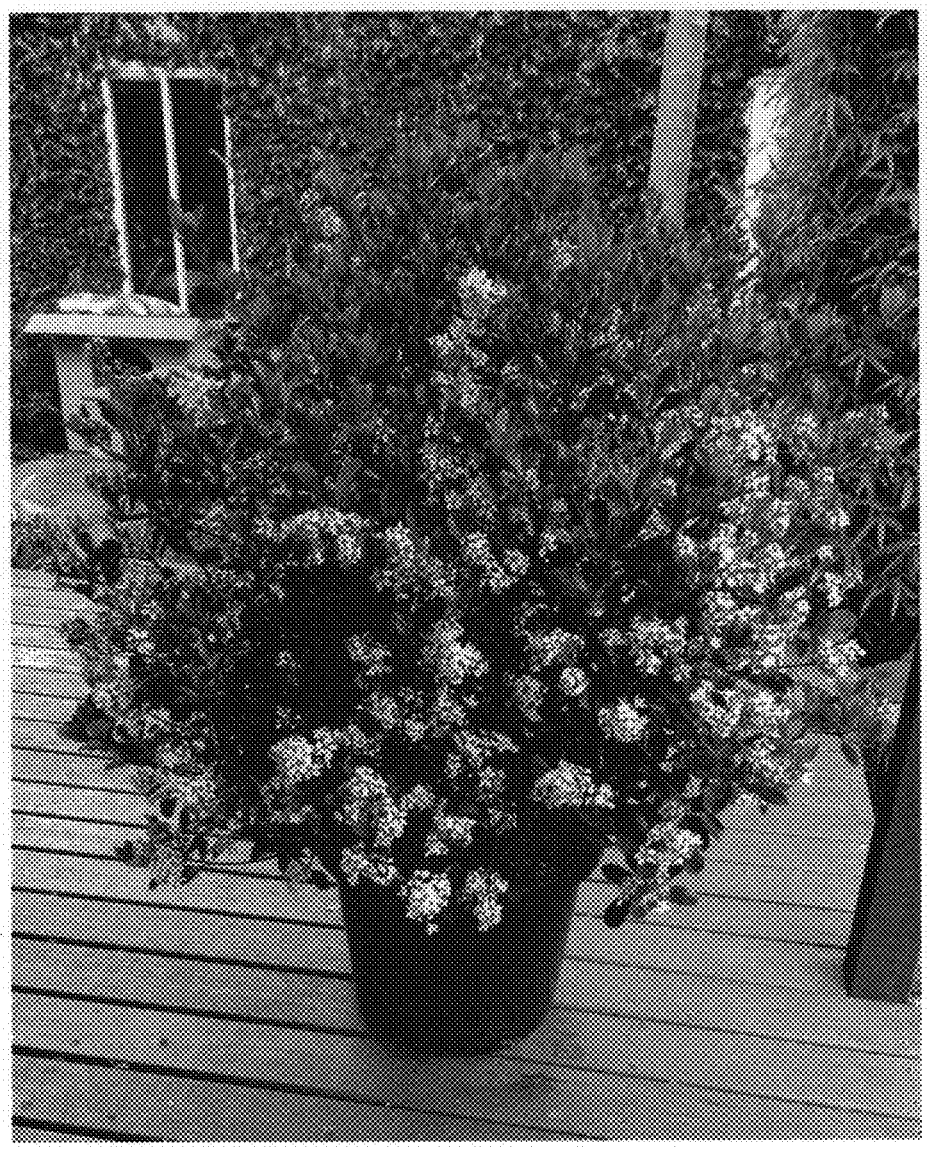
FIG. 2 shows a flowering plant of *Rhaphiolepis indica* 'PC2'.
Figure 3:
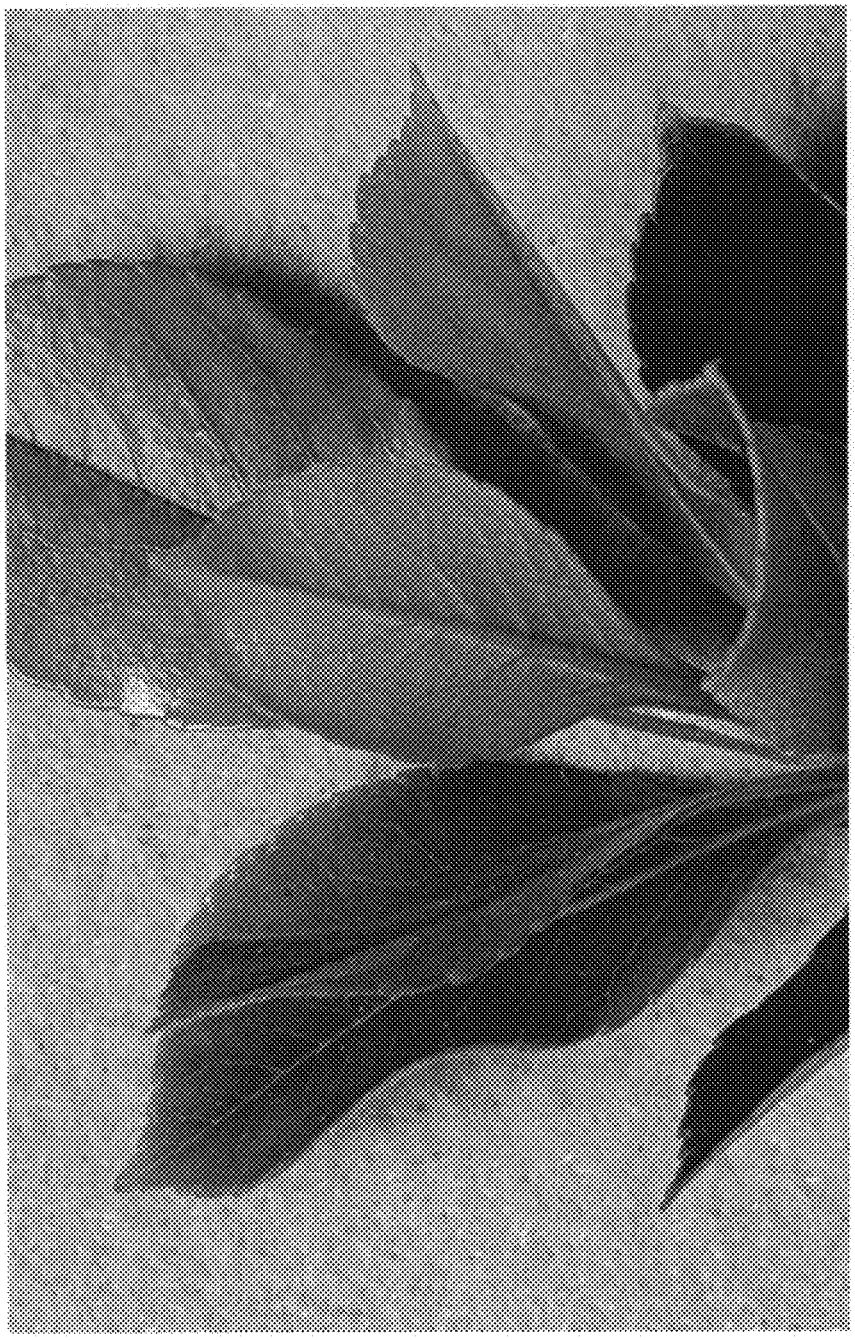
FIG. 3 shows a immature leaf color of *Rhaphiolepis indica* 'PC2'.
Figure 4:
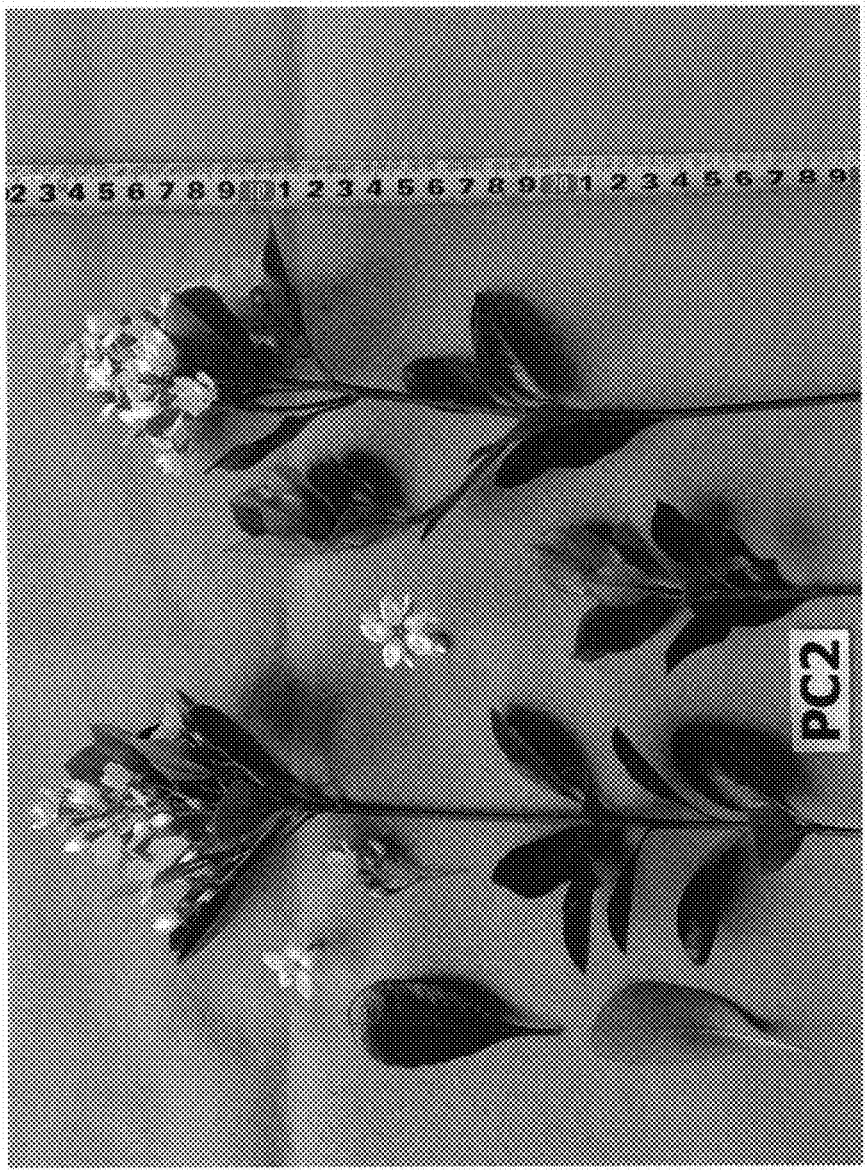
FIG. 4 shows stems, leaves, inflorescences and flowers of *Rhaphiolepis indica* 'PC2'.
Figure 5:
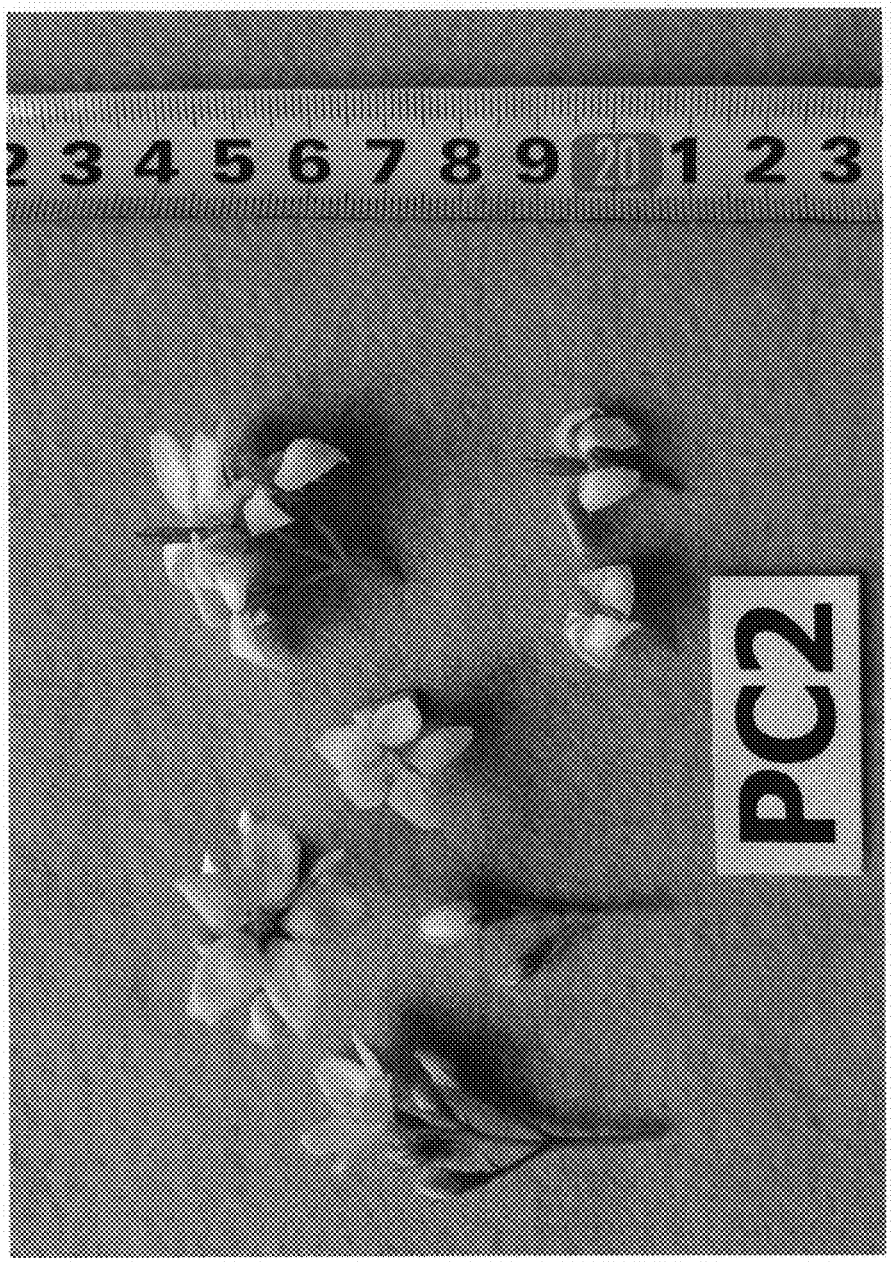
FIG. 5 shows the flower detail including petal, filament and calyx coloration of *Rhaphiolepis indica* 'PC2'.
Figure 6:
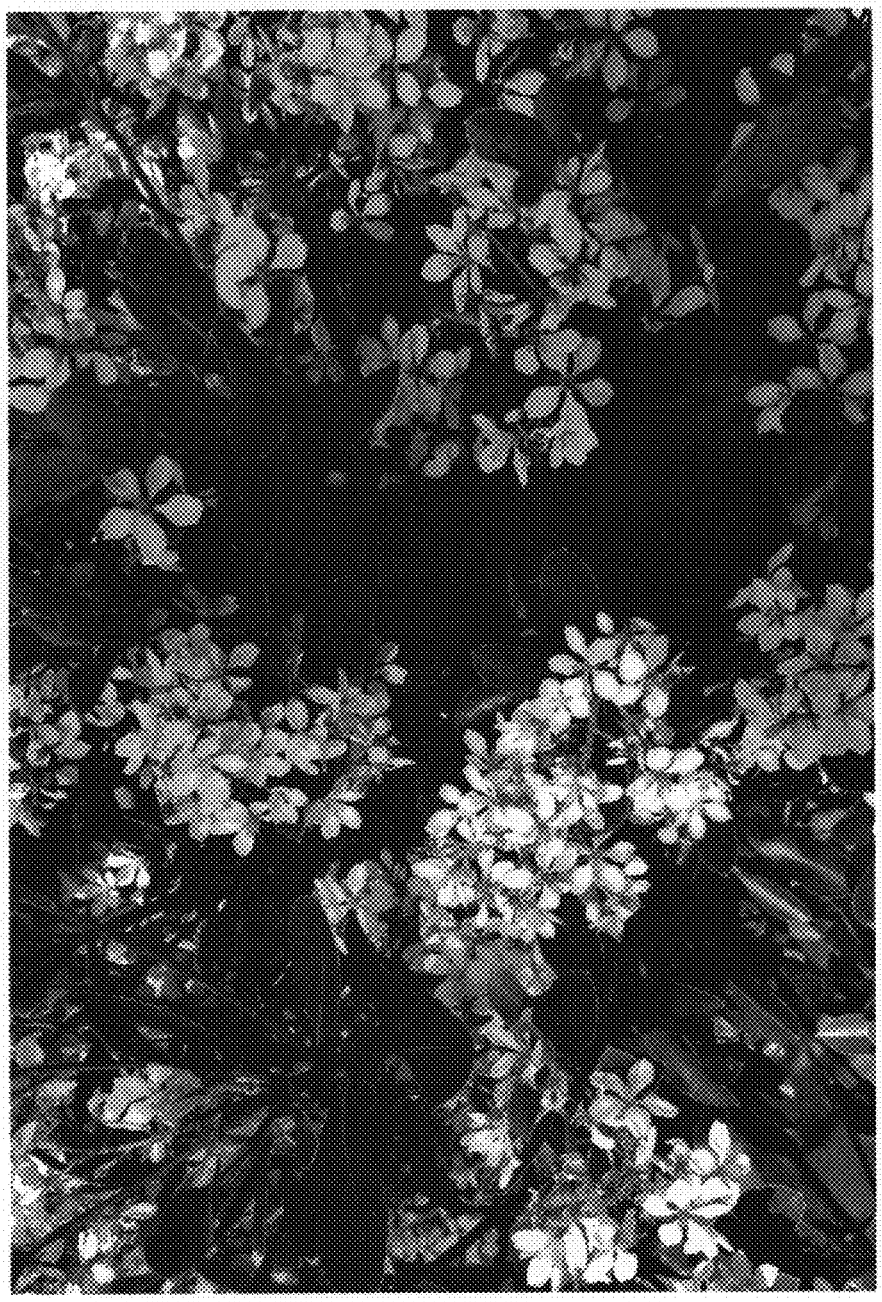
FIG. 6 shows full flowering of *Rhaphiolepis indica* 'PC2'.
Figure 7:
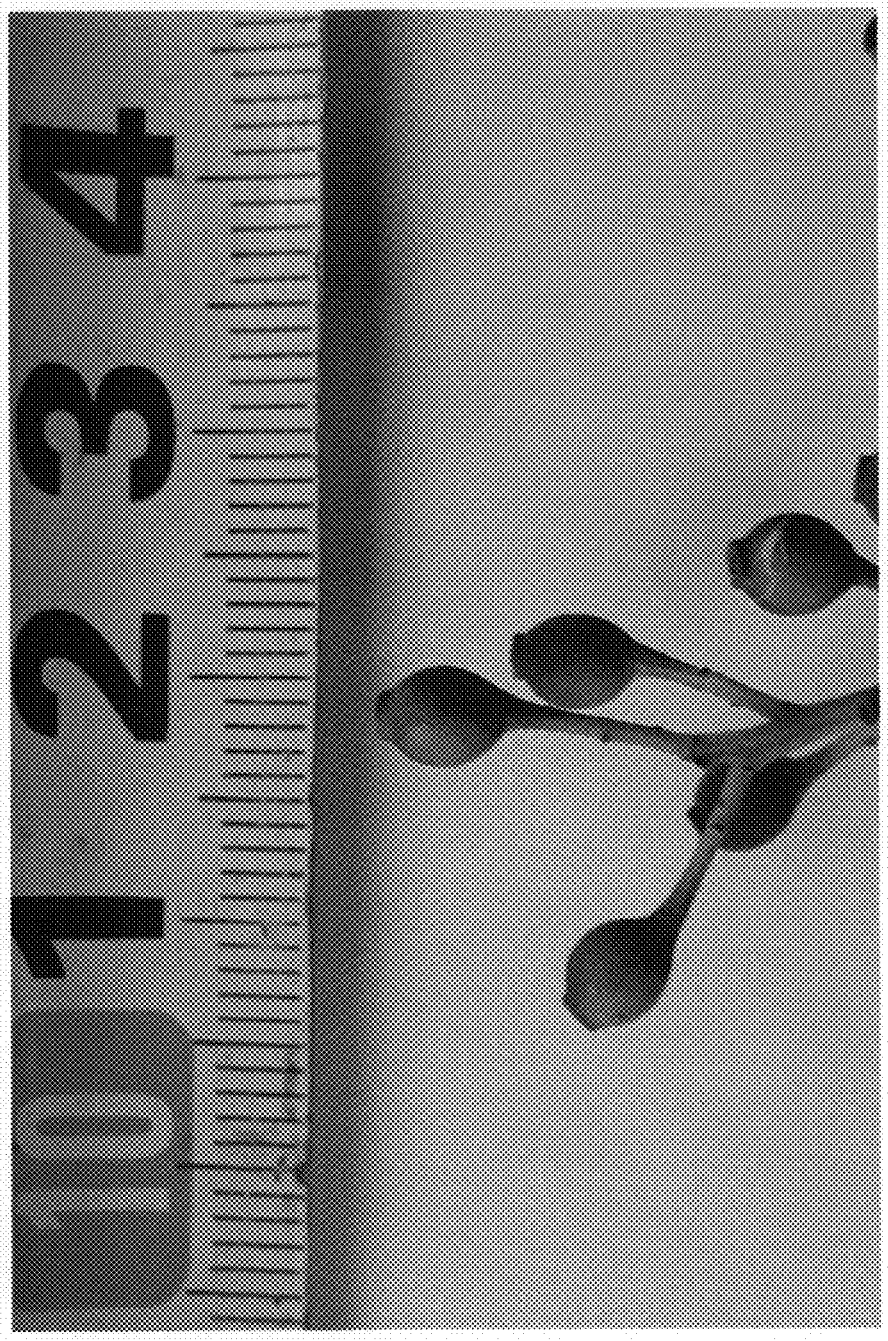
FIG. 7 shows fruit shape, size and color of *Rhaphiolepis indica* 'PC2'.

The following is a detailed botanical description of a new and distinct variety of *Rhaphiolepis indica* known as 'PC2' based upon observations of 24 month old plants grown in nursery pots in full sun in open beds in Laurieton, New South Wales, Australia during 2014-2015. Plant observations and descriptions were taken September 2015 to February 2016.

Those skilled in the art will appreciate that certain characteristics will vary with older or, conversely, with younger plants. 'PC2' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions.

Color notations are based on *The Royal Horticultural Society Colour Chart*, The Royal Horticultural Society, London, 2007 edition. A botanical description of 'PC2' and comparisons with the parent form of *Rhaphiolepis* indica and other cultivars are provided below.

Plant characteristics: Growth habit bushy with upright growth, height medium (to 1 m at maturity), width medium (to 1 m). Branch density is strongly dense.

Stems: The new stem has a smooth surface texture. The newly emerged stem color is grayed orange (RHS 177B). Semi-mature stem color is gray-brown (RHS 199A). Mature stem (hardwood) color is a composite of gray-brown (approximately RHS N199A), brown (RHS N200A) and gray (RHS 201A). Internode length on current season growth is short to medium range 10-15 mm. First year width is 2-3 mm, with a length of 9-15 cm. Second year width is 5-6 mm, with a length of 9-15 cm.

Leaves: Attitude semi-erect, arrangement alternate, mature length long (range 60 to 75 mm), mature width broad (range 27 to 35 mm), immature upper and lower side leaf color grayed orange (RHS 177B to 177C), partly mature leaf upper side color yellow green (RHS 146B), partly mature leaf lower side color yellow green (RHS 146D), mature leaf upper side color yellow green (approximately RHS 147A) with medium to strong surface glossiness, mature leaf lower side color yellow green (RHS 147B to 146B), variegation absent, leaf shape elliptic to obovate, leaf apex acuminate, leaf base attenuate, shape of cross section flat, shape of longitudinal axis straight, incision of margin present, depth of incision shallow and type of incision serrate, margin undulation very weak, upper side midrib prominence medium, upper side midrib color yellow green (RHS 146B), lower side midrib prominence strong, lower side midrib color yellow green (RHS 146B), venation pinnate and corresponding to leaf color, petiole length medium (range 4 to 7 mm), mature leaf petiole color yellow green (RHS 147A).

Inflorescence: Flowering season is late winter to spring. Inflorescence of 'PC2' has a panicle length 6 to 7 cm and width 5 to 7.5 cm, number of flowers to 22, peduncle length 4.0 cm, width 6 mm, peduncle color yellow green (RHS 144C), peduncle surface slightly hairy.

Flowers: Flower buds are elliptic, length is 4 to 7 mm, bud width is approximately 3 mm, flower bud color is red-purple (RHS73C) and changes to white (RHS NN155C) as petals mature. Flowers of 'PC2' are single with erect attitude, fragrance absent to very weak, flower diameter medium (range 27 to 28 mm). Petal color begins Red-Purple 73C, maturing to white (RHS NN155D), number of petals is 5, petal length 10-12 mm, petal width 5 mm, petal shape obovate, margin slightly fringed with apex ranging from acute to occasionally rounded and base often asymmetrical, pedicel color is yellow green (RHS 152C-D), pedicel length is 7-11 mm, diameter 2 mm. Calyx: 5 sepals, attitude reflexed, length 6 mm, diameter 3 mm, color of calyx base grayed purple (RHS 185A), color of margins and central part grayed yellow (RHS 161D). Individual flower duration is 2-3 weeks.

Reproductive organs: Stamens about 8 per flower, length 7 mm, stamen color grayed purple (RHS 186C) aging to grayed purple (RHS184C), anther shape oval, length 0.5 mm, width less than 0.5 mm, anther color yellow (RHS 11D), filament color white (RHS NN155D). Pistils: stigma and style number 2, fused at base, 8 mm longer, stigma rounded, stigma color white (RHS N155C), Style color green white (RHS 157D).

Fruits: Fruit color is yellow green (approximately RHS 152B) with anthocyanin coloration on sun exposed side commonly grayed purple (RHS 187A). Fruit shape is globose and size approximately 5 mm long by 4 mm wide. Fruit frequently abscise before maturation. Seed number is one, seed shape is globose, seed color is brown (RHS 200C-D) and seed diameter is 2.5 to 3.5 mm. Rate of seed set is very low (<1%).

Cold and heat tolerance: 'PC2' has not yet been observed under all conditions. The phenotype may vary somewhat with variations in environment such as temperature and light intensity, without any variance in genotype. 'PC2' is heat tolerant. It adapted well to the high heat conditions greater than 40 degrees Celsius maximum temperature during summer in Laurieton, New South Wales, Australia without any noticeable damage. Testing for environmental tolerances is ongoing, lowest temperature tolerance is not yet known.

Drought tolerance: Good drought tolerance typical of the species once established. Prefers moist conditions, can survive wet conditions with adequate drainage, but not boggy conditions. 'PC2' has not yet been observed under all conditions. Testing for environmental tolerances is ongoing.

Pest resistance: Resistance to pests is typical of the species. Observed resistant to *Entomosporium* leaf spot disease.

Cultural conditions: 'PC2' can tolerate low nutrient conditions; it does not like continually wet soil conditions, but can tolerate well-draining sandy soils to very heavy clay soils.

That which is claimed is:

1. A new and distinct *Rhaphiolepis indica* plant named 'PC2', substantially as described and illustrated herein.

* * * * *